(12) United States Patent
Bhurani et al.

(10) Patent No.: US 11,854,691 B1
(45) Date of Patent: *Dec. 26, 2023

(54) SYSTEMS AND METHODS FOR HANDS-FREE USER INTERFACES FOR HOSPITAL MANAGEMENT SYSTEMS

(71) Applicant: TeleTracking Technologies, Inc., Pittsburgh, PA (US)

(72) Inventors: Deepak Bhurani, Pittsburgh, PA (US); Manoj Kamavarapu, Pittsburgh, PA (US); Sagar Cheekati, Pittsburgh, PA (US); Shane Torsell, Pittsburgh, PA (US); Clinton Wadley, Pittsburgh, PA (US)

(73) Assignee: TELETRACKING TECHNOLOGIES, INC., Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/844,363

(22) Filed: Jun. 20, 2022

Related U.S. Application Data (63) Continuation of application No. 16/166,994, filed on Oct. 22, 2018, now Pat. No. 11,367,524.

(Continued)

(51) Int. Cl.
*G16H 40/20* (2018.01)
*G16H 40/60* (2018.01)
*G10L 15/20* (2006.01)
*A61B 34/00* (2016.01)
*A61B 17/00* (2006.01)

(52) U.S. Cl.
CPC .............. *G16H 40/20* (2018.01); *A61B 34/25* (2016.02); *G10L 15/20* (2013.01); *G16H 40/60* (2018.01); *A61B 2017/00203* (2013.01); *A61B 2034/256* (2016.02)

(58) Field of Classification Search
CPC ........ G16H 40/20; G16H 40/60; A61B 34/25; A61B 2017/00203; A61B 2034/256; G10L 15/20
See application file for complete search history.

(56) References Cited

U.S. PATENT DOCUMENTS

| | | | | |
|---|---|---|---|---|
| 6,263,311 | B1 * | 7/2001 | Dildy | G10L 17/00 704/247 |
| 7,673,347 | B2 * | 3/2010 | James | G06F 21/84 726/28 |

(Continued)

*Primary Examiner* — Sheetal R Paulson
(74) *Attorney, Agent, or Firm* — Ference & Associates LLC (57) ABSTRACT

One embodiment provides a method including receiving natural language speech from a user. The method includes automatically converting the natural language speech into a text format and executing a function corresponding to the function portion of the natural language speech. The method includes translating data returned by executing the function into natural language, wherein the translating includes modifying sensitive information within the data returned by (i) changing a selected audible output device and output volume to prevent the at least one unauthorized user from hearing the data returned and (ii) modifying the data returned. The method also includes outputting the natural language via an audible output device. Other aspects are described and claimed.

20 Claims, 4 Drawing Sheets

Related U.S. Application Data

(60) Provisional application No. 62/575,361, filed on Oct. 20, 2017.

(56) References Cited

U.S. PATENT DOCUMENTS

| | | | | |
|---|---|---|---|---|
| 9,536,106 B2 * | 1/2017 | Fram | .................. | G06F 16/95 |
| 10,311,249 B2 * | 6/2019 | Sharifi | .................. | G06F 21/35 |
| 2015/0294089 A1 * | 10/2015 | Nichols | .................. | G16H 40/20 |
| | | | | 705/3 |
| 2016/0260436 A1 * | 9/2016 | Lemay | .................. | G10L 15/22 |

* cited by examiner

SYSTEMS AND METHODS FOR HANDS-FREE USER INTERFACES FOR HOSPITAL MANAGEMENT SYSTEMS

CROSS-REFERENCE TO RELATED APPLICATIONS

This application claims priority to co-pending U.S. patent application Ser. No. 16/166,994, filed Oct. 22, 2018, titled "Systems and Methods for Hands-Free User Interfaces for Hospital Management Systems," which claims priority from U.S. Provisional Application Ser. No. 62/575,361, filed Oct. 20, 2017, the contents of both of which are incorporated by reference herein.

TECHNICAL FIELD

The present disclosure is directed to the technical field of hands-free user interfaces. More particularly, disclosed embodiments are directed to interactive hands-free interface for interacting with a hospital management system.

BRIEF SUMMARY

Disclosed embodiments provide improvements in hands-free interfaces for hospital management systems.

In summary, one aspect provides a method, the method including: receiving, at a voice processing module of an interface of a hands-free device associated with a user, natural language speech from the user, wherein the natural language speech includes at least one command and at least one word other than the command; automatically converting, using the voice processing module, the natural language speech into a text format, wherein the converting includes splitting the natural language speech into a function portion corresponding to the command and an input portion corresponding to the at least one other word; based on the at least one command, executing, using an application of the hands-free device, a function corresponding to the function portion, wherein the executing the function includes executing the function with respect to the input portion; translating, using an output generating module of the hands-free device, data returned by executing the function into natural language, wherein the translating includes modifying, responsive to determining at least one unauthorized user is co-located with the user, sensitive information within the data returned, wherein the modifying sensitive information includes at least one of: (i) changing a selected audible output device and output volume to prevent the at least one unauthorized user from hearing the data returned and (ii) modifying the data returned by performing at least one of (a) replacing the sensitive information with generic wording and (b) omitting the sensitive information by rephrasing the data returned; and outputting, using the output generation module of the interface of the hands-free device, the natural language via an audible output device.

Another aspect provides a system, the system including: a hands-free device associated with a user; a processor operatively coupled to the hands-free device; a memory device that stores instructions that, when executed by the processor, causes the system to: receive, at a voice processing module of an interface of the hands-free device, natural language speech from the user, wherein the natural language speech includes at least one command and at least one word other than the command; automatically convert, using the voice processing module, the natural language speech into a text format, wherein the converting includes splitting the natural language speech into a function portion corresponding to the command and an input portion corresponding to the at least one other word; based on the at least one command, execute, using an application of the hands-free device, a function corresponding to the function portion, wherein the executing the function includes executing the function with respect to the input portion; translate, using an output generating module of the hands-free device, data returned by executing the function into natural language, wherein the translating includes modifying, responsive to determining at least one unauthorized user is co-located with the user, sensitive information within the data returned, wherein the modifying sensitive information includes at least one of: (i) changing a selected audible output device and output volume to prevent the at least one unauthorized user from hearing the data returned and (ii) modifying the data returned by performing at least one of (a) replacing the sensitive information with generic wording and (b) omitting the sensitive information by rephrasing the data returned; and output, using the output generation module of the interface of the hands-free device, the natural language via an audible output device.

A further aspect provides a product, the product including: a computer-readable storage device that stores executable code that, when executed by a processor, causes the product to: receive, at a voice processing module of an interface of a hands-free device associated with a user, natural language speech from the user, wherein the natural language speech includes at least one command and at least one word other than the command; automatically convert, using the voice processing module, the natural language speech into a text format, wherein the converting includes splitting the natural language speech into a function portion corresponding to the command and an input portion corresponding to the at least one other word; based on the at least one command, execute, using an application of the hands-free device, a function corresponding to the function portion, wherein the executing the function includes executing the function with respect to the input portion; translate, using an output generating module of the hands-free device, data returned by executing the function into natural language, wherein the translating includes modifying, responsive to determining at least one unauthorized user is co-located with the user, sensitive information within the data returned, wherein the modifying sensitive information includes at least one of: (i) changing a selected audible output device and output volume to prevent the at least one unauthorized user from hearing the data returned and (ii) modifying the data returned by performing at least one of (a) replacing the sensitive information with generic wording and (b) omitting the sensitive information by rephrasing the data returned; and output, using the output generation module of the interface of the hands-free device, the natural language via an audible output device.

The foregoing general description and the following detailed description are exemplary and explanatory only and are not restrictive of the claims.

BRIEF DESCRIPTION OF THE SEVERAL VIEWS OF THE DRAWINGS

The accompanying drawings, which are incorporated in and constitute a part of this specification, illustrate several embodiments and, together with the description, serve to explain the disclosed principles. In the drawings.

DETAILED DESCRIPTION

Reference will now be made in detail to exemplary embodiments, examples of which are illustrated in the accompanying drawing and disclosed herein. Wherever convenient, the same reference numbers will be used throughout the drawings to refer to the same or like parts.

In high-stress, fast-paced environments, such as hospitals or other medical facilities, efficiency and accuracy are essential for patient health and satisfaction. Further, in medical environments, such as operating rooms, recovery units, intensive care units, and/or laboratories it may not always be possible to view data or input data without using a device by either touching a keyboard or a touchscreen. In some environments, such as an operating room, a medical provider may wish to view patient data or to record patient data, such as recording information about a patient reaction to a drug administered during surgery. However, medical professionals are unable to interact directly with computers during surgery or while providing care due to concerns about maintaining sterile environments and equipment. In some situations, facilities cover input/output devices with transparent surgical curtains. However, devices covered with transparent curtains are often cumbersome, and increase the probability of typos. As another example, in an emergency room, in severe trauma cases a medical provider may not have time to input several commands into a device to check operating room availability. As another example, a laboratory technician working in a sterile hood may wish to check information regarding a certain sample that the technician is testing, but may not do so without stopping the testing, checking the information on a device, and re-sterilizing before resuming testing. Solutions to reduce the time it takes for medical providers to access information and to increase the situations in which medical providers may access information are essential for improving hospital or medical facility efficiency.

Disclosed embodiments provide an interface through which a medical professional or professionals may access vital hospital or patient information without interacting physically with a device. In one embodiment, a medical professional may speak a command into a microphone of a hands-free device. The hands-free device, and/or a server, may process and execute the command by accessing database information and outputting that database information, via a speaker, in a natural language format. For example, in an emergency room setting, a medical provider may dictate information into a microphone, such as, "Save patient information. Patient John Doe. Approximately 30 years old. Male. Motor vehicle accident. Possible pulmonary laceration. Transporting patient to emergency operating room 2." In this example, the hands-free device may identify one or more keywords and/or phrases, such as "Save patient data," which may prompt a hospital system to save the dictated information following the keyword in a database. For example, "Save patient data," may prompt a new file for the patient to be created in the hospital database. Keywords such as "patient name," "years old," and "transporting patient," may prompt the hospital database to format and save information in a pre-defined format, such as a table or chart, including the patient's name, age, and current location within the hospital. In some embodiments, the system may require additional validation of the dictated information to ensure accuracy.

In another example, a laboratory technician may be handling and preparing a tissue sample from a patient for a diagnostic test. While continuing the sample preparation, the technician may say, for example, "What are patient Jane Doe's current medications?" The system may identify keywords "patient" and "current medications" and query patient records for the requested information. In response the system output may broadcast "Patient Jane Doe is currently taking 5 mg tamoxifen per day. No other known medications." In some embodiments, the system may require further identifying information to access patient data, such as a patient ID number and/or specimen barcode number. Unlike traditional methods of recording dictation, disclosed embodiments do not require transcription of a recording and may take further action based on a dictation, for example, saving the dictation to a chart and sending the dictation to a specified device.

In a medical environment, privacy and security of patient data is required by the Health Insurance Portability and Accountability Act of 1996 (HIPAA). In some embodiments, the hands-free device may require users to authenticate themselves. Some methods of authentication may include, for example, voice, facial, and/or other biometric recognition. In some embodiments, the user may be required to dictate a temporary, secure password or code to obtain access to the device. In other embodiments, the hands-free device may include a radio-frequency identification RFID chip such that the device is only active when placed in a secure area of the medical facility that is only accessible by medical professionals. In other embodiments, a medical provider may be paired with a headset that allows them to interact with the hands-free device in such a way that the provider receives patient information through the headset.

In some embodiments, a system may be programmed with logic to distinguish between multiple speakers in a room and determine the number and identity of people in a room, such as by recognizing distinct voices associated with multiple individuals. In such embodiments, the system may be configured to recognize an identity of a first pre-registered individual, and determine a security access level associated with the first pre-registered individual. For example, if the system has determined that a profile for the first pre-registered individual indicates that the individual has complete access to patient data, then the system may output audible responses containing HIPAA protected data. However, if the first pre-registered individual's profile indicates that they are only allowed to access certain pieces of information in a patient record, then the system may modify responses to refrain from outputting medical data that is associated with a higher security clearance level. In some embodiments, the system may be configured to detect other individuals in a room, and vary the amount of sensitive information output by the system based on a profile associated with the second individual. For example, if the first detected individual is associated with a highest security clearance, and the second detected individual is associated with a lower security level, the system may modify an output of sensitive information to include only information that the second individual is authorized to access, simply because the second individual is located in the same room and may otherwise gain unauthorized access to sensitive information. In some embodiments, the system may determine that an unknown individual is located within a predetermined distance of the system microphone, by determining that an unknown voice is speaking. In such situations, the system may refrain from outputting any sensitive medical information until the unknown speaker is registered and associated with a sufficient security access level. In other embodiments, system 100 may select speakers (e.g., control individual speakers or headsets) and determine volume such that those without sufficient security access cannot hear, while those with appropriate security access levels can hear.

In some embodiments, individuals may wear badges with an encoding (e.g., RFID) corresponding to their clearance. Disclosed embodiments may read the badges as a redundant measure to identify the clearances in the room or train the system to know which voice is associated with which clearance level.

Figure 1:
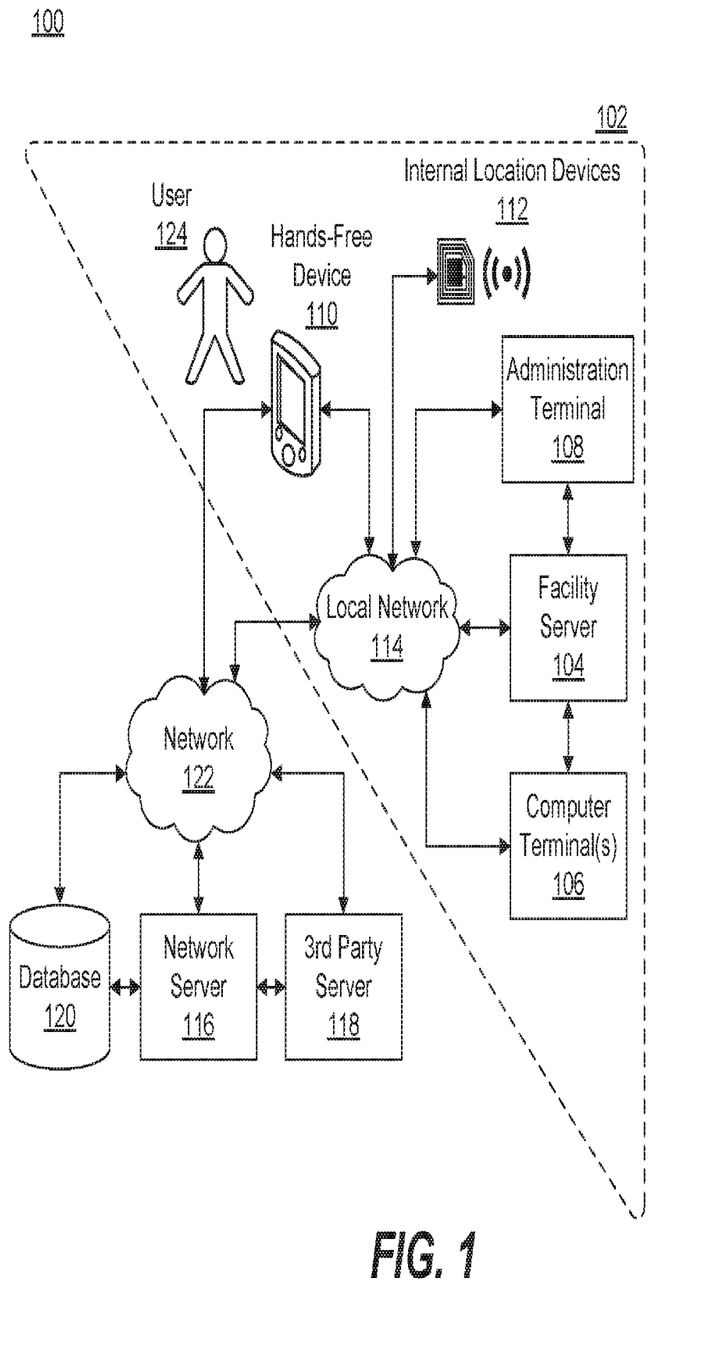
FIG. 1 shows a diagram of an exemplary computer system 100 configured to perform methods consistent with disclosed embodiments.

FIG. 1 shows a diagram of a computer system 100 that may be configured to perform one or more methods associated with hospital management and/or hospital optimization. The components and arrangements shown in FIG. 1 are not intended to limit the disclosed embodiments, as the components used to implement the disclosed processes and features may vary.

As shown in FIG. 1, system 100 may include facility system 102 and other external components. Facility system 102 may include facility server 104, computer terminal 106, administration terminal 108, hands-free device 110, and internal location devices 112. Elements in facility system 102 may communicate through local network 114. Additionally, system 100 may also include components external to the facility system 102. For example, system 100 may include network server 116, third party server 118, and external database 120. External elements may communicate with facility system 102 directly, through network 122, through local network 114, or through a combination of communications methods.

In some embodiments, local network 114, facility server 104, computer terminal 106, administration terminal 108, and hands-free device 110 may be physically disposed within a facility such as a hospital or office building (i.e. as facility system 102). Further, computer terminal 106 and administration terminal 108 may be two independent machines or a single machine with virtual or emulated partitions.

In some embodiments, components in facility system 102 and may connect to hands-free device 110, network 122, network server 116, third party server 118, and database 120. These elements may be external to the other facilities, may be contained in a single facility, or may be in a combination of facilities. Other components known to one of ordinary skill in the art may be included in system 100 to perform tasks consistent with the disclosed embodiments. For example, in some embodiments, facility system 102 may include one or more sensor devices such as sensors located throughout the facility to monitor one or more conditions such as occupancy, temperature, humidity, proximity, and other parameters indicative of a status or condition of a room, area, equipment, or supplies.

Computer terminal 106 may be a standalone device disposed in an office, a room, an employee station, or an alternative central location in a workplace. In some embodiments, computer terminal 106 may be a desktop or notebook computer, a flat panel or projected display, touch screen monitor, or any other display. In some embodiments, computer terminal 106 may be associated with a particular room in a facility, such as a particular patient room, hotel room, conference room, or any other type of room. Thus, a message or task request received from a computer terminal 106 may automatically associate the task request or message with the room in which computer terminal 106 is installed.

Administration terminal 108 may include a computer system or device associated with a user 124 that manages or oversees a portion of facility system 102. For example, administration terminal 108 may comprise a computer system located at a head nurse station, a housekeeping manager's office, or any other department manager's office or station.

User 124 may include one or more individuals who have an authorization to access information through system 100. User 124 may include any professional that may have authorization to access information about one or more patients. In some embodiments, user 124 may gain access by verbally providing a security code and/or code word, or via a voice recognition system. In some other embodiments, user 124 may be registered in a list of authorized users. Other authentication methods to access patient information, which are compliant with HIPAA regulations, may also be utilized to have user 124 connected to system 100.

User 124 may be an individual with a relationship with facility system 120. For example, user 124 may be an employee in a workplace environment such as a physician, nurse, technician, supervisor, manager, support personnel, dispatcher, or any other individual involved with facility system 102. User 124 may operate hands-free device 110, and/or another computer (not shown) to interact with system 100. System 100 may include multiple types of users such as, for example, patients, caregivers, technicians, task requestors, receptionists, and responders.

Hands-free device 110 may be a personal computing device capable of receiving audio input such as, for example, a general purpose or notebook computer, a mobile device with computing ability, a tablet, smartphone, wearable device such as Google Glass™ or smart watches, smart speaker such as Amazon Echo™ or Google Home™, or any combination of these computers and/or affiliated components. In some embodiments, hands-free device 110 may be a computer system or mobile computer device that is operated by user 124. In some embodiments, hands-free device 110 may be associated with a particular individual such as user 124, such that authentication services correlate devices and users. Hands-free device 110 may support an intelligent virtual assistant such as Apple Siri™, Amazon Alexa™, Google Assistant™, or Microsoft Cortana™.

In some embodiments, hands-free device 110 may communicate with facility server 104, computer terminal 106, and/or administration terminal 108 via direct wireless communication links (not shown), or via a combination of one or more of local network 114 and/or network 122.

Facility server 104 may be operated by a facility such as a hospital, business, retail location, and the like. Facility server 104 may also be operated by a contractor and/or a software service provider. Facility server 104 may enable communication within a computer-based system including computer system components such as desktop computers, workstations, tablets, hand held computing devices, memory devices, and/or internal network(s) connecting the components.

Network 122 may comprise any type of computer networking arrangement used to exchange data. For example, network 122 may be the Internet, a private data network, virtual private network using a public network, and/or other suitable connection(s) that enables system 100 to send and receive information between the components of system 100. Network 122 may also include a public switched telephone network ("PSTN") and/or a wireless cellular network.

Local network 114 may comprise any type of computer networking arrangement used to exchange data in a localized area, such as WiFi, Bluetooth™, Ethernet, and other suitable short-range connections that enable computer terminal 106, facility server 104, and hands-free device 110, to send and receive information between the components of system 100. In some embodiments, local network 114 may be excluded, and connected elements may communicate with system 100 components via network 122. In some embodiments, connected components may communicate with one or more system 100 components via a direct wired or wireless connection. In some embodiments, local network 114 may be a portion of network 122 or an extension of network 122.

Network server 116, third party server 118, and database 120 may be one or more servers or storage services provided by an entity such as a provider of networking, cloud, or backup services. For example, in some embodiments, network server 116 may be associated with a cloud computing service such as Microsoft Azure™ or Amazon Web Services™. In such embodiments, network server 116 may include a plurality of geographically distributed computing systems executing software for performing one or more functions of the disclosed methods. Additionally, in some embodiments, third party server 118 may be associated with a messaging service, such as, for example, Apple Push Notification Service, Azure Mobile Services, or Google Cloud Messaging. In such embodiments, third party server 118 may handle the delivery of messages and notifications related to functions of the disclosed embodiments, such as task creation, task assignment, task alerts, and task completion messages and notifications.

In some embodiments, system 100 may include configurations that vary from the example shown in FIG. 1, which illustrates a facility system 102 working in concert with a cloud computing system including network server 116, third party server 118, and database 120. As a first variation, system 100 may include only facility system 102, and thus may exclude cloud computing components such as network server 116, third party server 118, and database 120. In such embodiments, facility system 102 may handle substantially all operations and functions of the present embodiments. As a second variation, system 100 may exclude components of facility system 102. For example, facility server 104, may be excluded from system 100. In such embodiments, a cloud computing system including network server 116, third party server 118, and/or database 120 may handle some or all computing and message-related functions of the disclosed embodiments. Alternatively or additionally, components may be merged.

Figure 2:
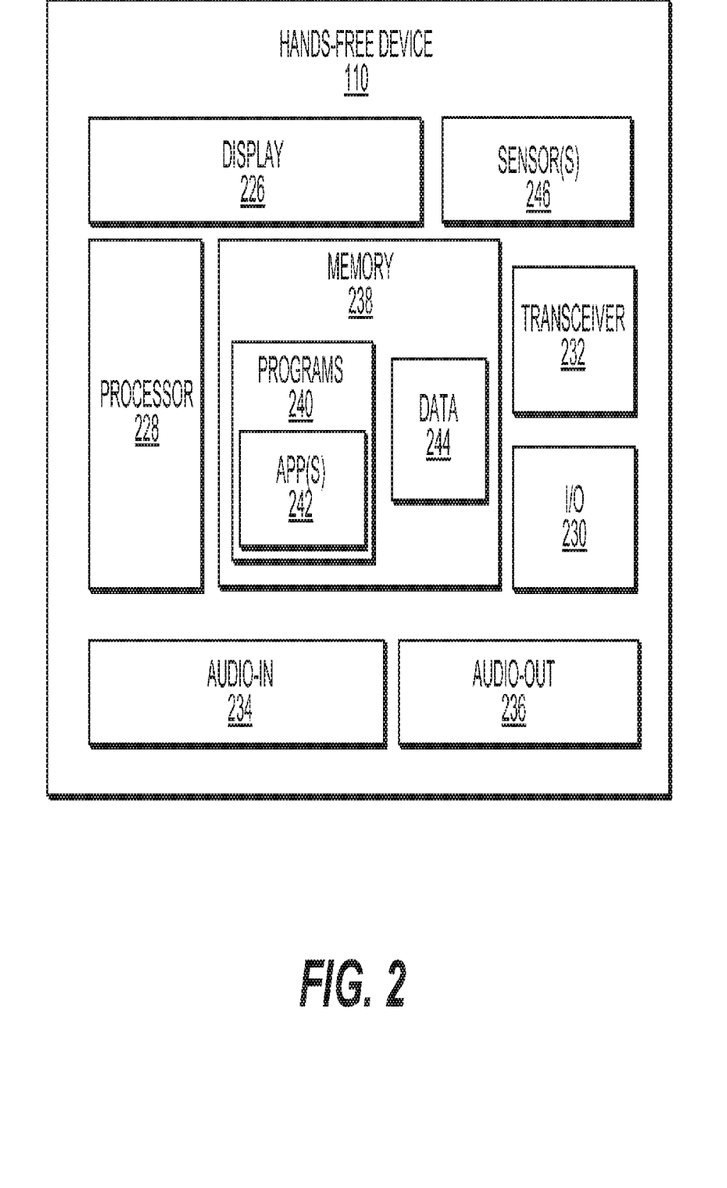
FIG. 2 shows a diagram of an exemplary hands-free device 110, consistent with disclosed embodiments.

FIG. 2 shows a diagram of hands-free device 110, consistent with disclosed embodiments. As shown, hands-free device 110 may include a display 226, one or more processors 228, input/output ("I/O") devices 230, a transceiver 232, audio input 234, audio output 236, and memory 238. In some embodiments a server, not shown, may execute one or more of the functions of hands-free device 110.

Display 226 may include one or more screens for displaying task management information such as, for example, liquid crystal display (LCD), plasma, cathode ray tube (CRT), or projected screens. In some embodiments, display 226 may be a separate device or may be the display of a computer terminal connected to the local network 114.

Processor 228 may be one or more known processing devices, such as microprocessors manufactured by Intel™ or AMD™ or licensed by ARM. Processor 228 may constitute a single core or multiple core processors that executes parallel processes simultaneously. For example, processor 228 may be a single core processor configured with virtual processing technologies. In certain embodiments, processor 228 may use logical processors to simultaneously execute and control multiple processes. Processor 228 may implement virtual machine technologies, or other known technologies to provide the ability to execute, control, run, manipulate, store, etc. multiple software processes, applications, programs, etc. In another embodiment, processor 228 may include a multiple-core processor arrangement (e.g., dual, quad core, etc.) configured to provide parallel processing functionalities to allow hands-free device 110 to execute multiple processes simultaneously. One of ordinary skill in the art would understand that other types of processor arrangements could be implemented that provide for the capabilities disclosed herein.

I/O devices 230 may include one or more devices that allow hands-free device 110 to receive input from a user. I/O devices 230 may include, for example, one or more pointing devices, keyboards, buttons, switches, touchscreen panels, cameras, barcode scanners, radio frequency identification (RFID) tag reader, and/or microphones. In some embodiments, hands-free device 110 may receive additional input from a user 124 via I/O devices 230, such as biometric information. In some embodiments, I/O devices 230 may be included on an additional device, such as a tablet, that is pair with the hands-free device 110 by a wireless or wired connection.

Transceiver 232 may include one or more communication modules for establishing communication between hands-free device 110 and other devices of system 100 via, for example, local network 114 and/or network 122. For example, transceiver 232 may include circuitry and one or more antennas for communicating wirelessly with local network 114 using a short range/near-field wireless communication protocol such as Bluetooth™, Bluetooth™ LE, WiFi, and Zigbee. Further, transceiver 232 may communicate with network 122 and/or local network 114 using any known network protocol including any form of wired or wireless internet access.

Audio-in 234 may include one or more microphones capable of receiving input or commands from user 124. In some embodiments, audio-in 234 may be a remote microphone connected to hands-free device 110 by a wired or wireless connection, such as Bluetooth™ Audio-out 236 may include one or more speakers capable of outputting sound to user 124. In some embodiments, audio-out 236 may be a remote speaker or speakers connected to hands-free device 110 by a wired or wireless connection, such as Bluetooth™. In some embodiments, audio-in 234 and audio-out 236 may be a device, such as a headset or earpiece, connected to the hands-free device 110 by a wired or wireless connection.

Memory 238 may include a volatile or non-volatile, magnetic, semiconductor, solid-state, tape, optical, removable, non-removable, or other type of storage device or tangible (i.e., non-transitory) computer-readable medium that stores one or more program(s) 240, such as app(s) 242, and data 244. Data 244 may include, for example, user information, task information, voice commands, and display settings and preferences. In some embodiments, data 244 may include one or more lists of voice commands associated with app(s) 242 and application functions.

Program(s) 240 may include operating systems (not shown) that perform known operating system functions when executed by one or more processors. By way of example, the operating systems may include Microsoft Windows™, Unix™, Linux™, Android™ and Apple™ operating systems, Personal Digital Assistant (PDA) type operating systems, such as Microsoft CE™, or other types of operating systems. Accordingly, disclosed embodiments may operate and function with computer systems running any type of operating system. Hands-free device 110 may also include communication software that, when executed by a processor, provides communications with network 122 and/or local network 114, such as Web browser software, tablet, or smart hand-held device networking software, etc.

Program(s) 240 may also include app(s) 242, such as a patient itinerary creation and management app, which when executed causes hands-free device 110 to perform processes related to receiving a voice command from a user 124, translating the voice command into a command or query executable by one or more app(s) 242, and/or processing a database query into natural language output to be broadcast by audio-out 236. For example, app(s) 242 may configure hands-free device 110 to receive a voice command to generate a patient itinerary, to provide a calculated itinerary for a patient, to output a real-time status of the patient's progress through the itinerary, identify potential delays or complications in patient care, to provide one or more alternative itineraries to mitigate the delays or complications, to receive instructions from one or more user 124. Furthermore, app(s) 242 may perform one or more automated tasks associated with the patient itinerary including, for example, generating one or more job tasks related to the patient itinerary based on the patient's status and progress, canceling and/or rescheduling one or more job tasks based on changes in the itinerary, requesting equipment or supplies associated with a task, and tracking the real-time status of all tasks related to the patient itinerary. In some embodiments, app(s) 242 may configure one or more computer systems to analyze historical patient itinerary data and hospital performance data to identify patterns, trends or correlative relationships in the historical data. For example, trends in historical data may indicate that certain patient diagnoses are associated with certain lengths of stay, or often experience delays and complications in certain portions of the itinerary. Historical data, identified trends and patterns, and correlative relationships may be identified through regression analysis, queuing analysis and other known statistical analysis methods, stored, and recalled during the creation and/or modification of new patient itineraries, to provide ever-improving patient care and efficiency. Correlations could be stored, retrieved and processed as Stochastic Information Packets (SIPs), Distribution Strings (DIST) or Stochastic Library Unit with Relationships Preserved (SLURPs). As discussed in further detail below, in some embodiments the implementation of these functions and the advantages realized by the present embodiments are attributed to the use of high-speed data and communication network, as well as personal communication and tracking devices disposed throughout a hospital.

In some embodiments, hands-free device 110 may contain one or more sensors 246 for collecting environmental, movement, location, and/or security data. Sensors 246 may include: one or more environmental sensors such as, for example, ambient light sensors, microphones, air pressure sensors, temperature sensors, and humidity sensors; motion detectors such as, for example, GPS receivers, location-based data receivers, accelerometers, and gyroscopes; and security sensors such as, for example, fingerprint readers, retina scanners, and other biometric sensors capable of use for security and individual identification. In some embodiments, processor 228 may use data collected by sensors 246 to control or modify functions of program(s) 240.

Figure 3:
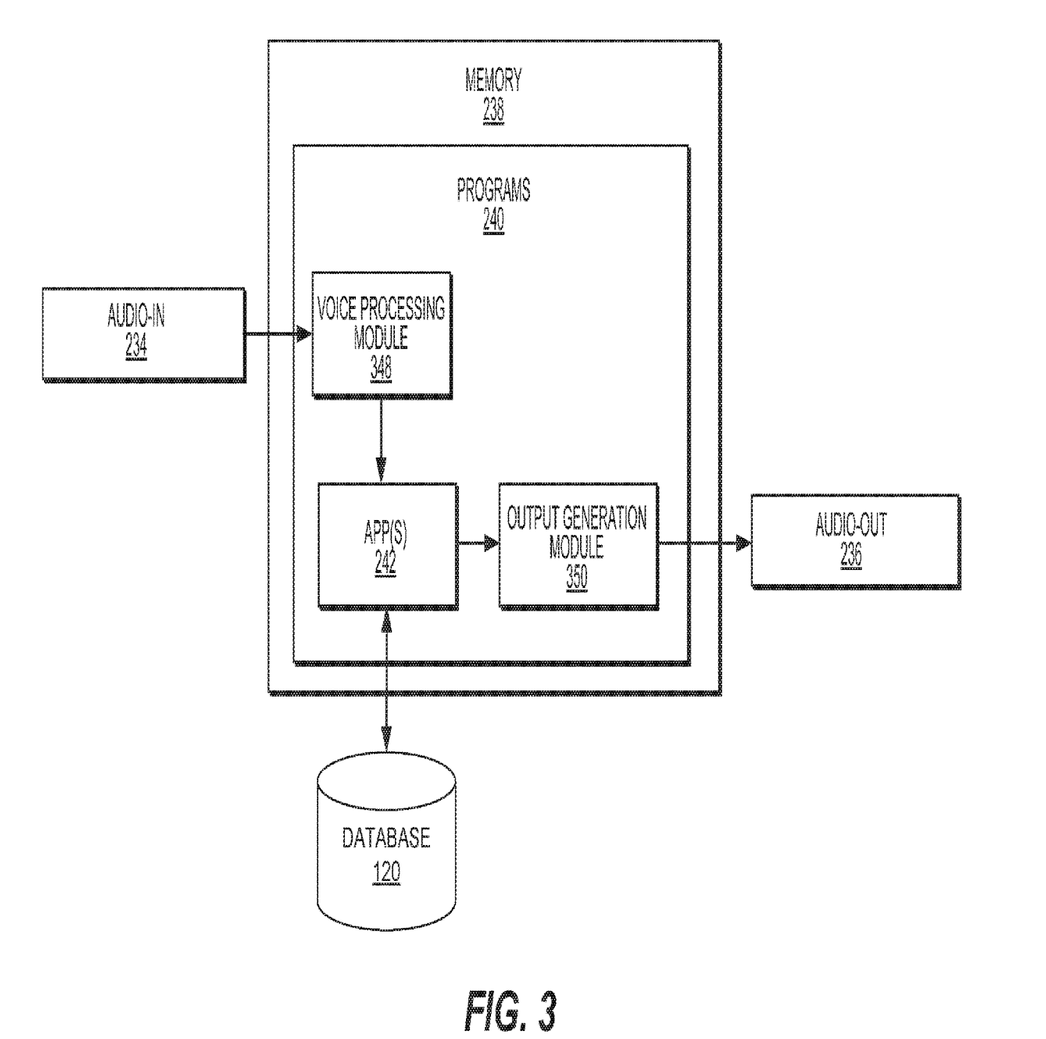
FIG. 3 shows a diagram of exemplary programs executed by hands-free device 110, consistent with embodiments of the present disclosure.

FIG. 3 is an exemplary configuration of hands-free device 110. In some embodiments, programs 240, stored in memory 238, may include a voice processing module 348 and output generation module 350.

Voice processing module 348 may be configured to receive voice input from user 124 via audio-in 234. In some embodiments, voice processing module 348 may not begin receiving a voice command until an initiation word is received by audio-in 234. For example, voice processing module 348 may not begin receiving and/or analyzing a voice command until a word and/or phrase such as "Initiate Hands-Free Device" is spoken by user 124 and received by audio-in 234. In some embodiments, voice processing module 348 may be initiated via I/O device 230 input or sensor 246 input by the user 124.

To maintain a secure transmission of patient and hospital data, voice processing module 348 may include one or more security or authentication steps before receiving voice command data from user 124. User 124 may be required to input biometric information via sensor(s) 246 to initiate access to hospital and patient information. In some embodiments, voice processing module 348 may use voice recognition to authenticate a user 124. In other embodiments, a user 124 may be required to input a security code or password via I/O device 230.

After a user 124 is authenticated and/or audio-in 234 detects the initiation word and/or phrase from user 124, the voice module 348 may begin receiving a spoken command from the user 124 via audio-in 234. In some embodiments, the spoken command may be one or more of a command from a pre-defined list of commands. In other embodiments, the command may be a natural language command or a combination of a pre-defined command and natural language. For example, the user 124 may initiate a command by saying, "Initiate hands-free device. Tell me the location of Patient John Doe at 3:00 pm." Voice processing module 348 may detect "Initiate hands-free device" and begin receiving the command "Tell me the location of Patient John Doe at 3:00 pm." The voice processing module 348 may initiate app functionality to query a database 120 to retrieve the data requested by the user 124.

Upon receiving a spoken command, voice processing module 348 may translate the voice command into a query or request to execute an app function. For example, voice processing module 348 may translate a natural language command into a structured query language and/or a language executable by processor 228.

In some embodiments voice processing module 348 may include speech-to-text translation capabilities. For example, voice processing module 348 may translate a user's dictation into a microphone into text and the text may be input into one or more apps 242 able to identify keywords and information within the text.

Once an executable command is generated by voice processing module 348, one or more apps 242 may execute the command for example, by retrieving data from a database, such as database 120. In some embodiments, voice processing module 348 translates speech into text and that text is received by app 242. In other embodiments, the one or more apps 242 may receive real-time data from the facility server 104, computer terminal 106, administration terminal 108, network server 116, and/or third-party server 118 via a network such as local network 114 and/or network 122. In some embodiments, the app 242 may require further spoken commands, for example, to navigate through a menu. Audio-out 236 may be configured to provide prompts to the user 124 indicative of required spoken commands.

After the app 242 generates data responsive to the user's spoken command and/or commands, the output generation module 350 may translate that data into natural language output. For example, the app 242 may query database 120 and receive output from the database 120 in the form of a table. Output generation module 350 may reconfigure the data in the returned table into a form that may be output as a natural language sentence via audio-out 236. For example, a query by app 242 responsive to the voice command "Tell me the location of Patient John Doe at 3:00 pm," is shown in Table 1:

TABLE 1

| | |
|---|---|
| Patient Name | John Doe |
| Intake Date | 2017 Oct. 16 05:00:00 |
| Symptoms at Intake | Arm pain, shortness of breath |
| Diagnosis | Myocardial Infraction |
| Administered treatment | IV fluids, aspirin, thrombolytic |
| Bed No. | 11234 |
| Bed Location | Coronary Care Unit |
| Scheduled Test 1 | Chest X-Ray |
| Scheduled Test Date 1 | 2017 Oct. 16 15:00:00 |
| Scheduled Test 1 Location | Coronary Care Unit, X-Ray Room 1 |
| Prescribing Physician | Dr. Jane Smith |

In this example, information in addition to the data shown in Table 1 may be returned. Output generation module 350 may then format the data from Table 1 into a natural language sentence, such as "Patient Doe will be in x-ray room 1 in the coronary care unit at 3:00 pm." In this example, the sentence may then be broadcast via audio-out 236, giving the user 124 the requested data.

In some embodiments, the hands-free device 110 may be modified to be HIPAA compliant. For example, output generation module 350 may be configured to omit confidential patent information. In some embodiments, in response to a request by a user 124 for confidential information, the output generation module 350 may output a phase such as, "You are requesting to access restricted information. Please modify request." In some embodiments, the user 124, who has previously been authenticated, may be prompted to speak a pre-configured device address, such as for a specific computer terminal 106 to which confidential data may be sent and displayed. This method allows the user 124 to request confidential data to be displayed on a specified device without physically touching a device. In some embodiments, the user 124 may also request, for example, that patient monitoring data recorded during a surgery be saved and sent to a patient's file.

Figure 4:
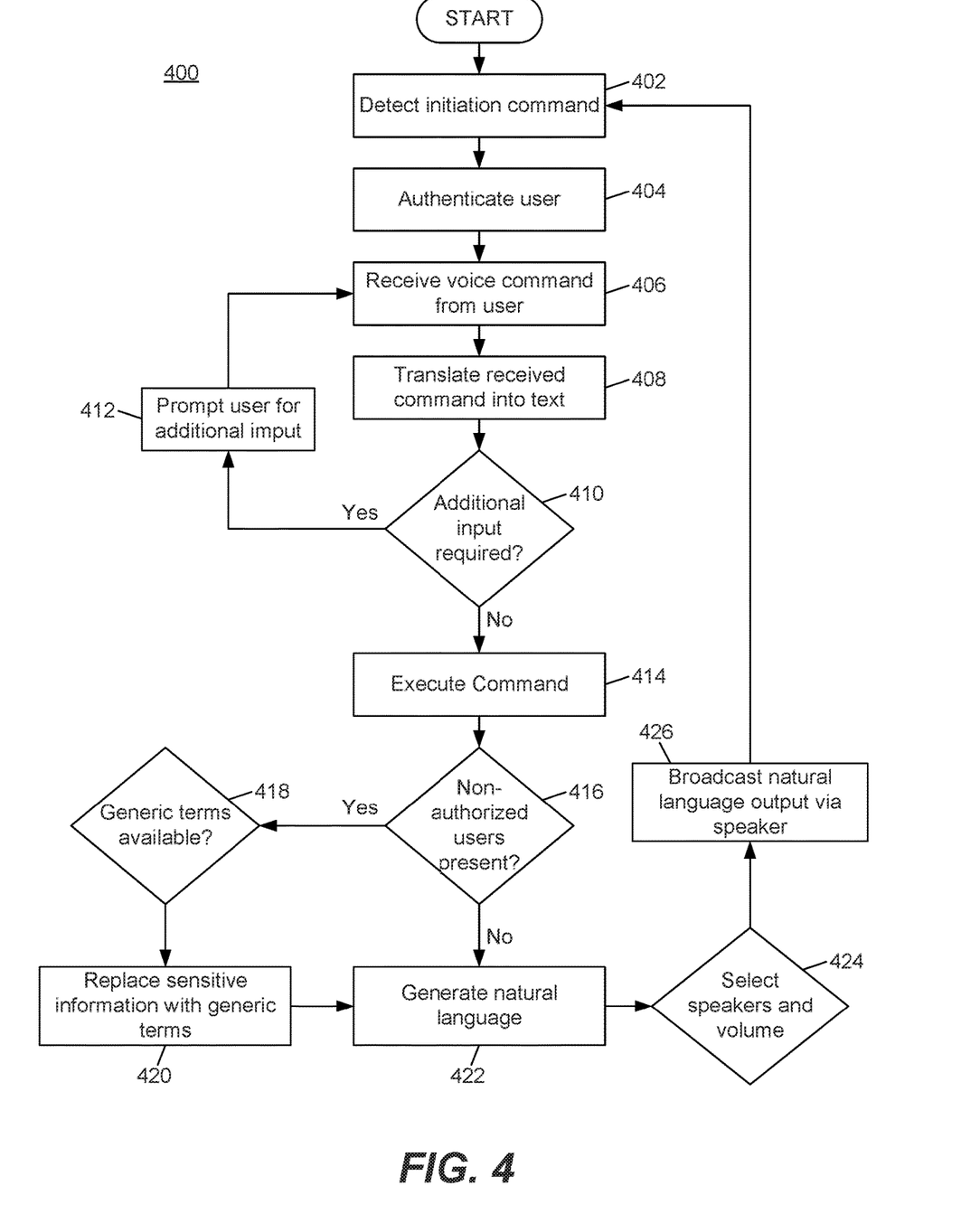
FIG. 4 depicts an example of a flowchart for providing data via a hands-free device, consistent with embodiments of the present disclosure.

FIG. 4 is a flow chart of an exemplary process 400 for executing, by the hands-free device 110, a command from user 124. The microphone to the hands-free device 110, e.g., audio-in 234, may detect an initiation command spoken by the user 124 (step 402). In some embodiments, the initiation command may be received via sensors 246 and/or I/O device 230. Responsive to the initiation command, the hands-free device 110 may authenticate the user 124 (step 404). For example, user 124 may be prompted to recite a user ID and/or password. If the user 124 does not provide a correct user ID and/or password, the user may be prompted to attempt a different method of authentication, for example, a biometric identification (e.g., voice identification, facial recognition, retina scans). Hands-free biometric authentication mechanisms may be favorable in a healthcare environment to avoid sanitization issues. In some embodiments, system 100 may use one or more authentication mechanisms in combination, such as a passphrase, RFID badge (e.g., a physical authentication credential), and/or biometric authentication (e.g., voice identification). Therefore, merely speaking the passphrase while holding a security credential may allow system 100 to authenticate the user using three different mechanisms: a password (the spoken passphrase), biometric authentication (voice identification), and a physical credential (an RFID badge, for example).

Once the user 124 is authenticated, the hands-free device 110 may receive a spoken command from the user 124 (step 406). In some embodiments, speech-to-text translation may not be enabled until the microphone has received an activation word or phrase. As previously described, the spoken command may be processed and translated into text and/or a computer executable command associated with one or more functions (step 408). If any additional command and/or additional input is required by the user (step 410), the devise may prompt the user to dictate the additional input (step 412). When sufficient input is received, one or more processors may execute the received command. Executing the command may include one or more functions, for example, querying a database, saving dictated information to a specified location, displaying information from a database, and/or sending information from a database to another device to be displayed.

Once the command is executed, a processor may determine whether unauthorized users are present (step 416). For example, system 100 may use voice recognition, proximity sensors, RFID sensors, and/or real-time location sensing devices to count and/or identify individuals in a room. When unauthorized users are present (e.g., step 416, "yes"), system 100 may determine whether it can replace confidential or private information using generic wording (or rephrasing to omit those private information). For example, system 100 may query a database with the sensitive information. Based on the query, system 100 may receive FIIPAA-compliant generic terms that abstract details of the patient information. Rather than indicating that a patient has a particular disease, a FIIPAA compliant database may indicate a class of disease or relevant characteristics of the disease that need not be kept private. When generic terms are available, system 100 may replace those sensitive terms with generic terms (step 420). Alternatively, system 100 may omit sensitive information (e.g., responsive to determining that no generic terms are available). Next, a processor may format the data into natural language text, for example, using output generation module 350 (step 422). System 100 may determine which speakers to output the audio and the volume at which to play the audio (step 424). For example, system 100 may select speakers (e.g., control individual speakers or headsets) and determine volume such that those without sufficient security access cannot hear, while those with appropriate security access levels can hear. In some embodiments, system 100, responsive to determining that unauthorized users (or one or more users with unknown authorization statuses) are present, system 100 may determine to play audio over headsets of authorized users when headsets are worn. Text-to-speech translation may then be used to output the natural language text via one or more speakers (step 426).

Although not shown in FIG. 4, process 400 may return to receive a subsequent command from a user (e.g., return to step 406) after broadcasting audio on one or more speakers.

In some embodiments, however, system 100 may automatically time-out authentication if not in use. When no activity occurs (e.g., return to step 402), system 100 may require that a user re-authenticate to resume interacting with it. For example, when authenticated using real-time location sensing and/or voice authentication, system 100 may timeout after 5-10 seconds, or one minute. When a user is authenticated through a web portal, system 100 may time out after 10-30 minutes, such as 12 minutes, for example.

Additionally and/or alternatively to providing natural language audio output, disclose embodiments may control one or more devices. For example, system 100 may transmit commands to devices that are connected to a network and/or have an interface (e.g., an application programming interface (API)) to provide commands. Example devices controlled by system 100 using process 400 include motorized beds, heating and/or cooling in a room, blood pressure monitoring cuffs, devices controlling intravenous (IV) medicine dosing. For example, a user may request a blood pressure reading using process 400 and system 100 may initiating the blood pressure cuff and provide the results of the reading (e.g., in step 426). As another example, a user may request a bed move from a lay-flat position to an upright position, and system 100 may follow process 400 to execute that command (e.g., in step 414). Additional devices and commands may be used to interact with other controllable devices in a healthcare facility or other context.

Disclosed embodiments may override security in certain situations. For example, in an emergency situation, system 100 may provide information without authentication or regard to timeout. As an example, in response to receiving audio of a person speaking "code blue" repeatedly, system 100 may provide secure information so that emergency care can be facilitated. In other embodiments, system 100 may allow an authorized user to decide whether to display or share private information. For example, system 100 may guide or warn the user whether or not to be careful about sharing information (e.g., inadvertently sharing) based on detected proximate individuals.

The foregoing description has been presented for purposes of illustration. It is not exhaustive and is not limited to the precise forms or embodiments disclosed. Modifications and adaptations of the embodiments will be apparent from consideration of the specification and practice of the disclosed embodiments. For example, the described implementations include hardware, firmware, and software, but systems and methods consistent with the present disclosure can be implemented as hardware alone.

Computer programs based on the written description and methods of this specification are within the skill of a software developer. The various programs or program modules can be created using a variety of programming techniques. For example, program sections or program modules can be designed in or by means of Java, C, C++, assembly language, or any such programming languages. One or more of such software sections or modules can be integrated into a computer system, non-transitory computer-readable media, or existing communications software.

Moreover, while illustrative embodiments have been described herein, the scope includes any and all embodiments having equivalent elements, modifications, omissions, combinations (e.g., of aspects across various embodiments), adaptations or alterations based on the present disclosure. Further, the steps of the disclosed methods can be modified in any manner, including by reordering steps or inserting or deleting steps.

What is claimed is:

1. A method, the method comprising:
   receiving, at a voice processing module of an interface of a hands-free device associated with a user, natural language speech from the user, wherein the natural language speech comprises at least one command and at least one word other than the command;
   automatically converting, using the voice processing module, the natural language speech into a text format, wherein the converting comprises splitting the natural language speech into a function portion corresponding to the command and an input portion corresponding to the at least one other word;
   based on the at least one command, executing, using an application of the hands-free device, a function corresponding to the function portion, wherein the executing the function comprises executing the function with respect to the input portion;
   translating, using an output generating module of the hands-free device, data returned by executing the function into natural language, wherein the translating comprises modifying, responsive to determining at least one unauthorized user is co-located with the user, sensitive information within the data returned, wherein the modifying sensitive information comprises at least one of: (i) changing a selected audible output device and output volume to prevent the at least one unauthorized user from hearing the data returned and (ii) modifying the data returned by performing at least one of (a) replacing the sensitive information with generic wording and (b) omitting the sensitive information by rephrasing the data returned; and
   outputting, using the output generation module of the interface of the hands-free device, the natural language via an audible output device.

2. The method of claim 1, wherein the at least one command is identified via a keyword within the natural language speech.

3. The method of claim 1, wherein the voice processing module receives authentication information from at least one sensor of the hands-free device before accepting the natural language speech.

4. The method of claim 1, wherein the text format corresponds to a text format of a database and wherein the text format is executable within the database.

5. The method of claim 4, wherein the executing comprises executing the function within the database.

6. The method of claim 1, wherein the translating comprises including, responsive to determining no unauthorized user is co-located with the user, the sensitive information within the data returned.

7. The method of claim 1, further comprising authenticating the user, wherein the authenticating the user comprises:
   receiving biometric data via one or more sensors associated with the user; and
   verifying the biometric data matches stored biometric data associated with the user; and wherein the translating is responsive to the authenticating.

8. The method of claim 1, further comprising authenticating the user, wherein the authenticating the user comprises:
   receiving a user identification and a password associated with the user; and
   verifying the user identification and password match a stored user identification and password associated with the user; and
   wherein the translating is responsive to the authenticating.

9. The method of claim 1, further comprising:
receiving location data from one or more sensors;
comparing the location data with data indicating allowed operation areas within a facility; and
disabling, responsive to determining the location data indicates the device is not within an allowed operation area, the hands-free device.

10. The method of claim 1, prompting the user to dictate one or more subsequent commands.

11. A system, the system comprising:
a hands-free device associated with a user;
a processor operatively coupled to the hands-free device;
a memory device that stores instructions that, when executed by the processor, causes the system to:
receive, at a voice processing module of an interface of the hands-free device, natural language speech from the user, wherein the natural language speech comprises at least one command and at least one word other than the command;
automatically convert, using the voice processing module, the natural language speech into a text format, wherein the converting comprises splitting the natural language speech into a function portion corresponding to the command and an input portion corresponding to the at least one other word;
based on the at least one command, execute, using an application of the hands-free device, a function corresponding to the function portion, wherein the executing the function comprises executing the function with respect to the input portion;
translate, using an output generating module of the hands-free device, data returned by executing the function into natural language, wherein the translating comprises modifying, responsive to determining at least one unauthorized user is co-located with the user, sensitive information within the data returned, wherein the modifying sensitive information comprises at least one of: (i) changing a selected audible output device and output volume to prevent the at least one unauthorized user from hearing the data returned and (ii) modifying the data returned by performing at least one of (a) replacing the sensitive information with generic wording and (b) omitting the sensitive information by rephrasing the data returned; and
output, using the output generation module of the interface of the hands-free device, the natural language via an audible output device.

12. The system of claim 11, wherein the at least one command is identified via a keyword within the natural language speech.

13. The system of claim 11, wherein the voice processing module receives authentication information from at least one sensor of the hands-free device before accepting the natural language speech.

14. The system of claim 11, wherein the text format corresponds to a text format of a database and wherein the text format is executable within the database.

15. The system of claim 14, wherein the executing comprises executing the function within the database.

16. The system of claim 11, wherein the translating comprises including, responsive to determining no unauthorized user is co-located with the user, the sensitive information within the data returned.

17. The system of claim 11, further comprising authenticating the user, wherein the authenticating the user comprises:
receiving biometric data via one or more sensors associated with the user; and
verifying the biometric data matches stored biometric data associated with the user; and wherein the translating is responsive to the authenticating.

18. The system of claim 11, further comprising authenticating the user, wherein the authenticating the user comprises:
receiving a user identification and a password associated with the user; and
verifying the user identification and password match a stored user identification and password associated with the user; and
wherein the translating is responsive to the authenticating.

19. The system of claim 11, further comprising:
receiving location data from one or more sensors;
comparing the location data with data indicating allowed operation areas within a facility; and
disabling, responsive to determining the location data indicates the device is not within an allowed operation area, the hands-free device.

20. A product, the product comprising:
a non-transitory computer-readable storage device that stores executable code that, when executed by a processor, causes the product to:
receive, at a voice processing module of an interface of a hands-free device associated with a user, natural language speech from the user, wherein the natural language speech comprises at least one command and at least one word other than the command;
automatically convert, using the voice processing module, the natural language speech into a text format, wherein the converting comprises splitting the natural language speech into a function portion corresponding to the command and an input portion corresponding to the at least one other word;
based on the at least one command, execute, using an application of the hands-free device, a function corresponding to the function portion, wherein the executing the function comprises executing the function with respect to the input portion;
translate, using an output generating module of the hands-free device, data returned by executing the function into natural language, wherein the translating comprises modifying, responsive to determining at least one unauthorized user is co-located with the user, sensitive information within the data returned, wherein the modifying sensitive information comprises at least one of: (i) changing a selected audible output device and output volume to prevent the at least one unauthorized user from hearing the data returned and (ii) modifying the data returned by performing at least one of (a) replacing the sensitive information with generic wording and (b) omitting the sensitive information by rephrasing the data returned; and
output, using the output generation module of the interface of the hands-free device, the natural language via an audible output device.

* * * * *